(12) United States Patent
Kawata et al.

(10) Patent No.: US 7,156,834 B2
(45) Date of Patent: Jan. 2, 2007

(54) DISPOSABLE BODY FLUID ABSORBENT PAD

(75) Inventors: Hikari Kawata, Kagawa-ken (JP); Masashi Nakashita, Kagawa-ken (JP); Kaori Yamauchi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 408 days.

(21) Appl. No.: 10/669,910

(22) Filed: Sep. 24, 2003

(65) Prior Publication Data

US 2004/0064123 A1 Apr. 1, 2004

(30) Foreign Application Priority Data

Sep. 27, 2002 (JP) ............................. 2002-283242

(51) Int. Cl.
*A61F 13/20* (2006.01)
(52) U.S. Cl. ...................................... 604/392; 604/387
(58) Field of Classification Search .......... 604/385.01, 604/385.03, 385.14, 385.21, 386–387, 389, 604/391–393
See application file for complete search history.

(56) References Cited

U.S. PATENT DOCUMENTS

| | | | | |
|---|---|---|---|---|
| 3,871,378 A | * | 3/1975 | Duncan et al. | 604/372 |
| 4,745,926 A | * | 5/1988 | Hlusko | 128/873 |
| 5,651,779 A | * | 7/1997 | Burrell | 604/395 |
| 5,700,256 A | | 12/1997 | Yamamoto et al. | |
| 6,368,313 B1 | * | 4/2002 | Howard | 604/385.09 |
| 6,895,901 B1 | * | 5/2005 | Howard | 119/869 |
| 2004/0074450 A1 | * | 4/2004 | Soares et al. | 119/850 |

FOREIGN PATENT DOCUMENTS

| | | |
|---|---|---|
| EP | 0 617 941 | 10/1994 |
| JP | 2000-262556 | * 9/2000 |
| JP | 2002-119528 A | 4/2002 |
| WO | WO 98 20824 | 5/1998 |
| WO | WO 02 069868 | 9/2002 |

* cited by examiner

*Primary Examiner*—Michele Kidwell
(74) *Attorney, Agent, or Firm*—Butzel Long

(57) ABSTRACT

A disposable body fluid absorbent pad comprises a liquid-pervious topsheet, a liquid-impervious backsheet, a liquid-absorbent core interposed between these sheets and a strap adapted to pull the pad in a longitudinal direction. The strap comprises first and second straps attached to transversely opposite side edge margins of the pad, respectively, so to extend outward from an end margin of a front region. These first and second straps have inner fixed portions fixed to the topsheet, outer fixed portions fixed to the backsheet and hand-grips extending between the inner fixed portions and the outer fixed portions, respectively.

10 Claims, 15 Drawing Sheets

DISPOSABLE BODY FLUID ABSORBENT PAD

BACKGROUND OF THE INVENTION

The present invention relates to a disposable body fluid absorbent pad.

A disposable body fluid absorbent pad being longer than being wide is well known, which comprises a liquid-pervious topsheet facing a wearer's body, a liquid-impervious backsheet facing away from the wearer's body and a liquid-absorbent core interposed between these sheets and contoured by longitudinally opposite end margins extending in a transverse direction and transversely opposite side edge margins extending in a longitudinal direction.

The pad disclosed in Japanese Patent Application Publication No. 2002-119528A has a front region destined to cover a wearer's belly, a rear region destined to cover a wearer's hip and an intermediate region destined to cover a wearer's crotch. This pad is provided on its backsheet with a ring-shaped rubber member. Specifically, the rubber member is provided in a transversely middle zone in the intermediate region of the pad in a manner that longitudinally opposite ends of the rubber member are secured to an outer surface of the backsheet and an intermediate portion extending between these opposite ends is let free from the outer surface of the backsheet. This pad is adapted to be laid on an inner side of shorts and put on a wearer's body together with the shorts. With this pad, the rubber member attached to the outer surface of the backsheet comes in contact with the inner side of the shorts and functions as anti-slip means to prevent the pad from slipping with respect to the shorts.

The pad disclosed in the above-cited Publication is adapted to be merely placed upon the shorts when the pad is put on the wearer's body, so the pad itself is not independently held in close contact with the wearer's body. It is essential to use the shorts to hold the pad in close contact with the wearer's body. As the shorts slips down along the wearer's waist, this pad moves away from the wearer's crotch and it is no more possible for the pad to absorb body fluids. Particularly when the pad is put on the bedridden wearer, the shorts must be first put on the wearer and then the pad must be placed upon the inner side of the shorts. Thus much time and labor should be necessary to put the pad on the wearer's body.

SUMMARY OF THE INVENTION

It is an object of the present invention to provide a disposable body fluid absorbent pad improved so that the pad can be placed in close contact with the wearer's body using no shorts and easily put on the wearer's body.

According to the present invention, there is provided a disposable body fluid absorbent pad comprising a top surface facing a wearer's body, a back surface facing away from the wearer's body and a liquid-absorbent core interposed between the top and back surfaces and being contoured by longitudinally opposite end margins extending in a transverse direction and transversely opposite side edge margins extending in a longitudinal direction and being relatively large in the longitudinal direction.

The improvement according to the present invention further comprises the pad having a front region destined to cover a wearer's belly, a rear region destined to cover a wearer's hip and an intermediate region destined to cover a wearer's crotch when the pad is put on the wearer's body, the pad including a strap adapted to pull the pad in the longitudinal direction and the strap having inner fixed portions lying on the side edge margins and secured to the pad on a surface facing the wearer's body and a hand-grip extending between the inner fixed portions.

The present invention includes the following embodiments.

The strap comprises a first strap attached to one of the side edge margins so as to extend outward from the end margin of the front region in the longitudinal direction and a second strap is attached to the other side edge margin so as to extend outward from the end margin of the front region in the longitudinal direction, the first strap having an inner fixed portion lying on one of the side edge margins and secured to the pad on the surface facing the wearer's body, an outer fixed portion lying on the other side edge margin and secured to the pad on the surface facing away from the wearer's body and a hand-grip extending between the inner fixed portion and the outer fixed portion and the second strap having an inner fixed portion lying on the other side edge margin and secured to the pad on said surface facing the wearer's body, an outer fixed portion lying on the other side edge margin and secured to the pad on the surface facing away from the wearer's body and a hand-grip extending between the inner fixed portion and the outer fixed portion.

The inner fixed portions of the straps extend from the end margin of the front region toward the end margin of the rear region along the side edge margins.

The elastic members extending in the side edge margins of the pad in the longitudinal direction are attached to the front, rear and intermediate regions, at least to the intermediate region of the pad so that the elastic members are contractible in the longitudinal direction and the inner fixed portions of the straps shrink in the longitudinal direction as the elastic members contract.

The straps are elastically stretchable and the inner fixed portions of the straps are secured to the pad on the surface facing the wearer's body so that the inner fixed portions are contractible.

The top and back surfaces are defined by a liquid-pervious topsheet and a liquid-impervious backsheet, respectively.

The thickness dimension of the core between the top and back surfaces as measured in the intermediate region is smaller than that of as measured in the front and rear regions.

The transverse dimension of the core between the side edge margins as measured in the intermediate region is smaller than that of a measured in the front and rear regions.

The pad is provided in the rear region with a tape fastener having a proximal end fixed to the pad on the surface facing away from the wearer's body in the rear region and a distal end extending outward from the end margin of the rear region in the longitudinal direction and adapted to be releasably attached to the pad on the surface facing away from the wearer's body.

The intermediate region of the pad is folded in the longitudinal direction with the topsheet inside so that the front and rear regions may be placed upon each other and then the distal end of the tape fastener is releasably attached to the pad on the surface facing away from the wearer's body in the front region so as to maintain the pad in a folded state.

DETAILED DESCRIPTION OF THE PREFERRED EMBODIMENTS

Details of the disposable body fluid absorbing pad according to the present invention will be more fully understood from the description given hereunder with reference to the accompanying drawings.

Figure 1:
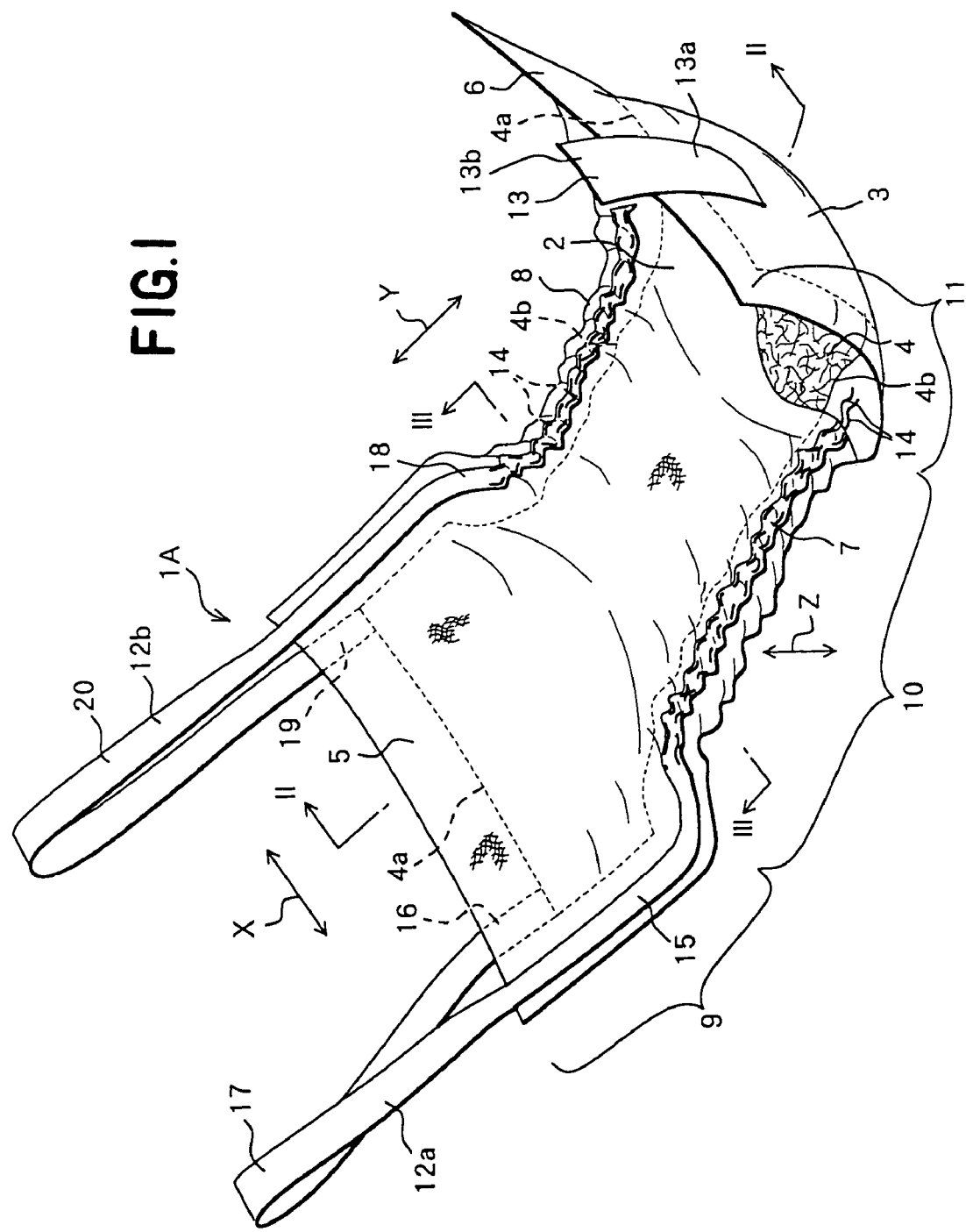
FIG. 1 is a partially cutaway perspective view showing a typical embodiment of a pad according to the invention.
Figure 2:
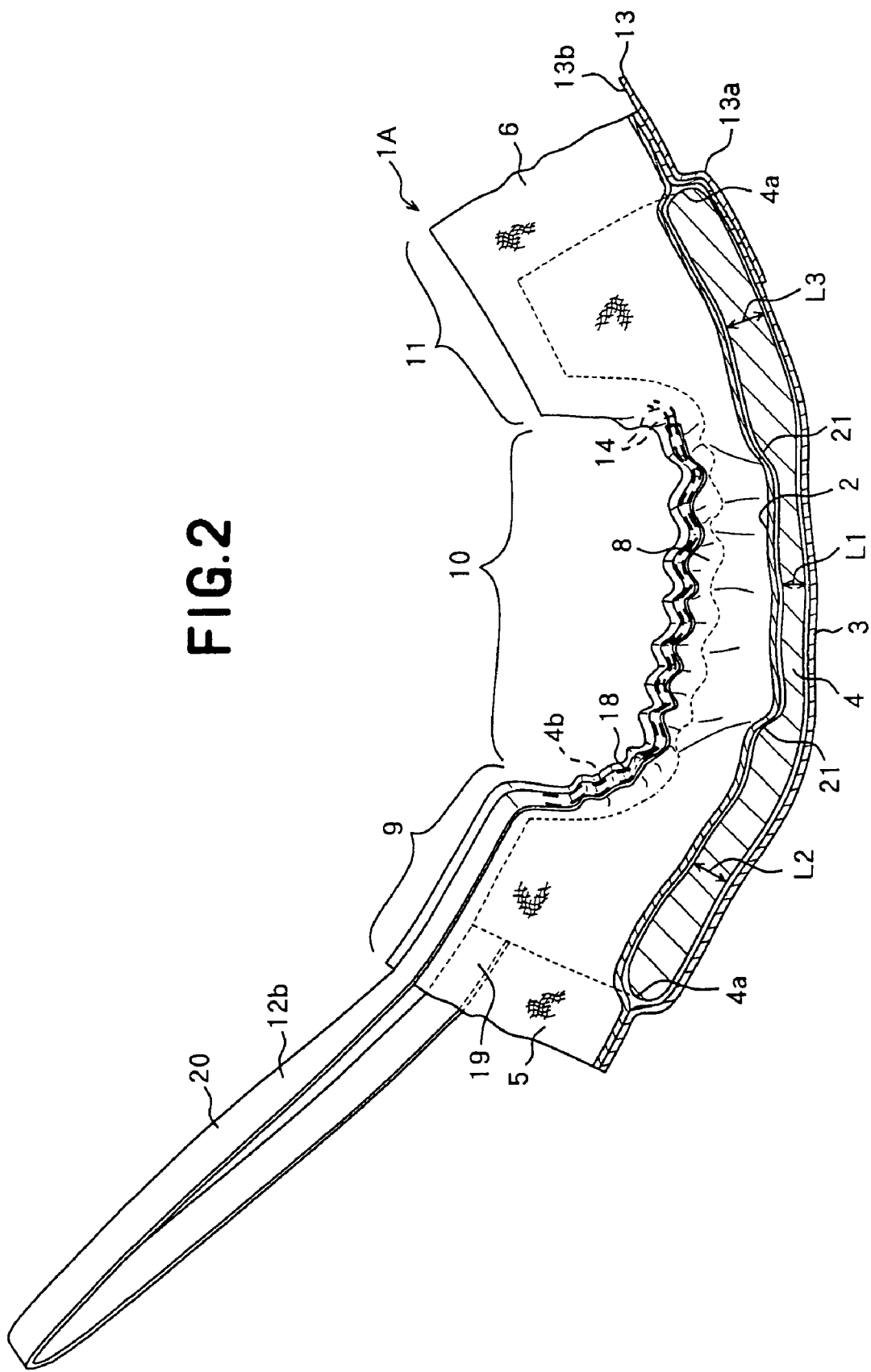
FIG. 2 is a sectional view taken along a line II—II in FIG. 1.
Figure 3:
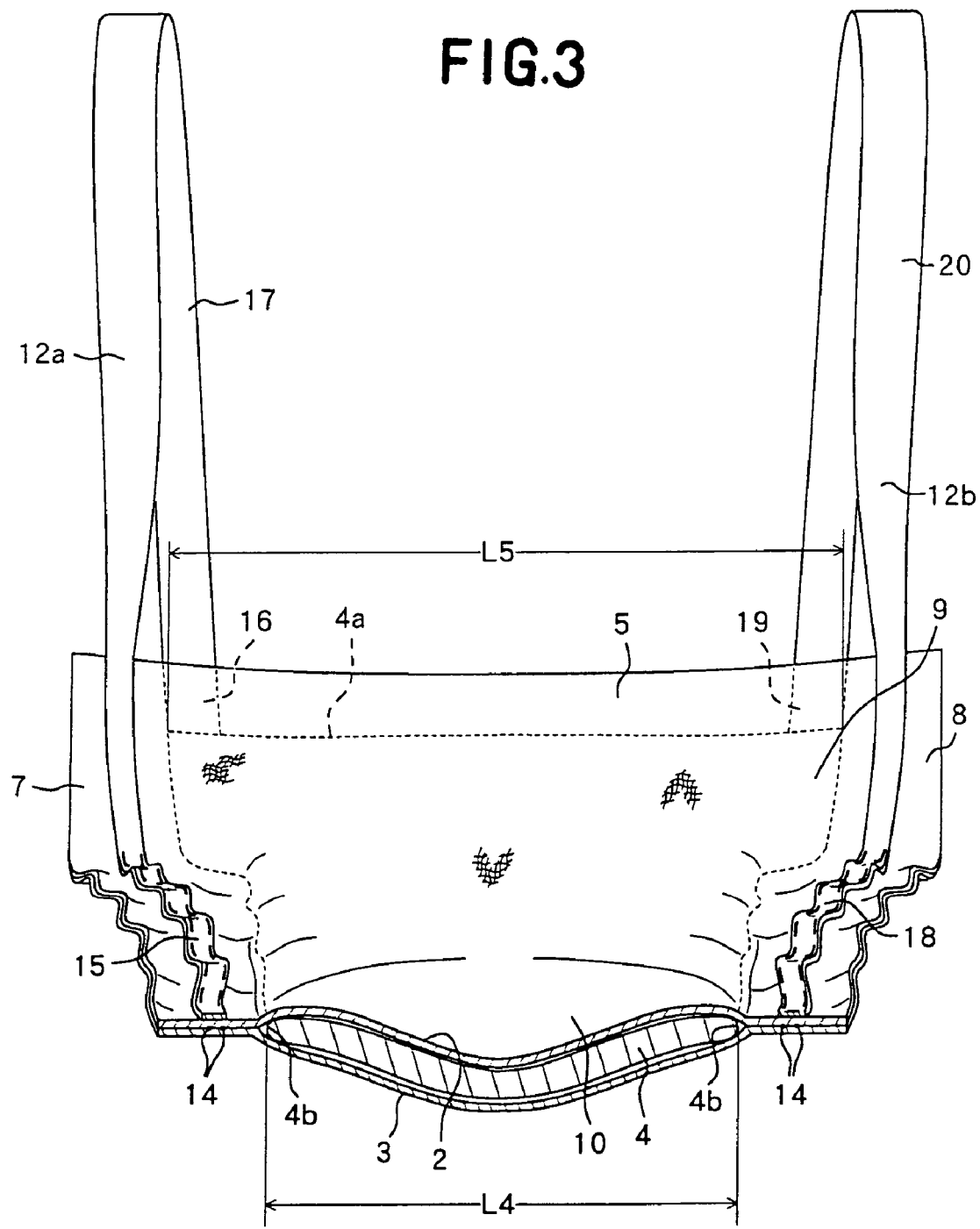
FIG. 3 is a sectional view taken along a line III—III in FIG. 1.

FIG. 1 is a partially cutaway perspective view showing a pad 1A as a typical embodiment of the pad according to the invention, FIG. 2 is a sectional view taken along a line II—II in FIG. 1 and FIG. 3 is a sectional view taken along a line III—III in FIG. 1. In FIG. 1, a transverse direction is indicated by an arrow X, a longitudinal direction is indicated by an arrow Y and a thickness direction is indicated by an arrow Z. Expression "inner surfaces of top- and backsheets 2, 3" means the respective surfaces of these sheets 2, 3 facing a core 4 and expression "outer surfaces of these sheets 2, 3" means the respective surfaces of these sheets 2, 3 facing away from the core 4.

The pad 1A comprises the liquid-pervious topsheet 2 facing the wearer's body, the liquid-impervious backsheet 3 facing away from the wearer's body and the liquid-absorbent core 4 interposed between the top- and backsheets 2, 3. The pad 1A is relatively large in the longitudinal direction and includes longitudinally opposite end margins 5, 6 lying outside longitudinally opposite ends 4a of the core 4 so as to extend in the transverse direction and transversely opposite side edge margins 7, 8 lying outside transversely opposite side edges 4b of the core 4 so as to extend in the longitudinal direction.

Figure 4:
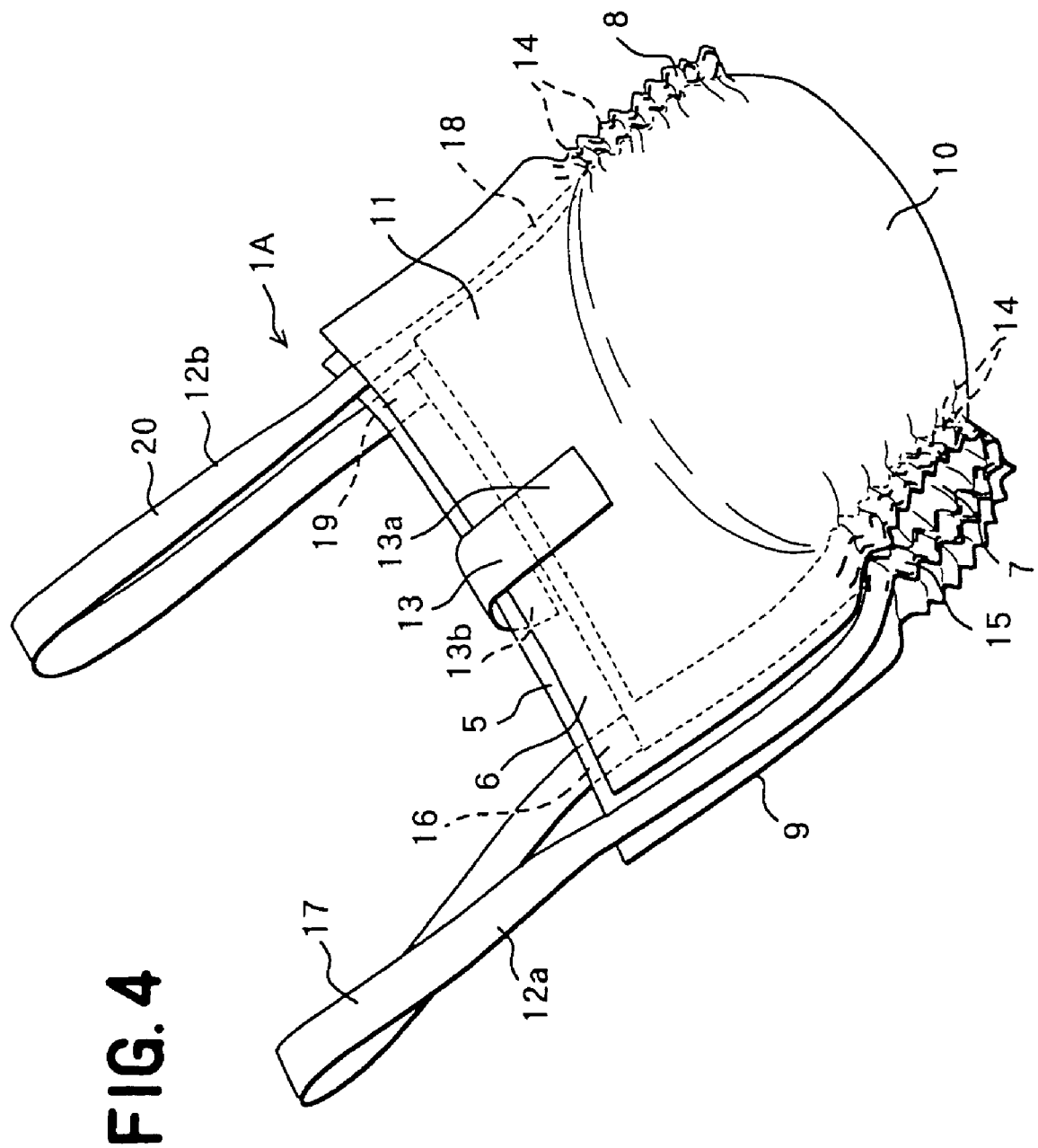
FIG. 4 is a perspective view showing the pad still in a folded state before actual use thereof.
Figure 5:
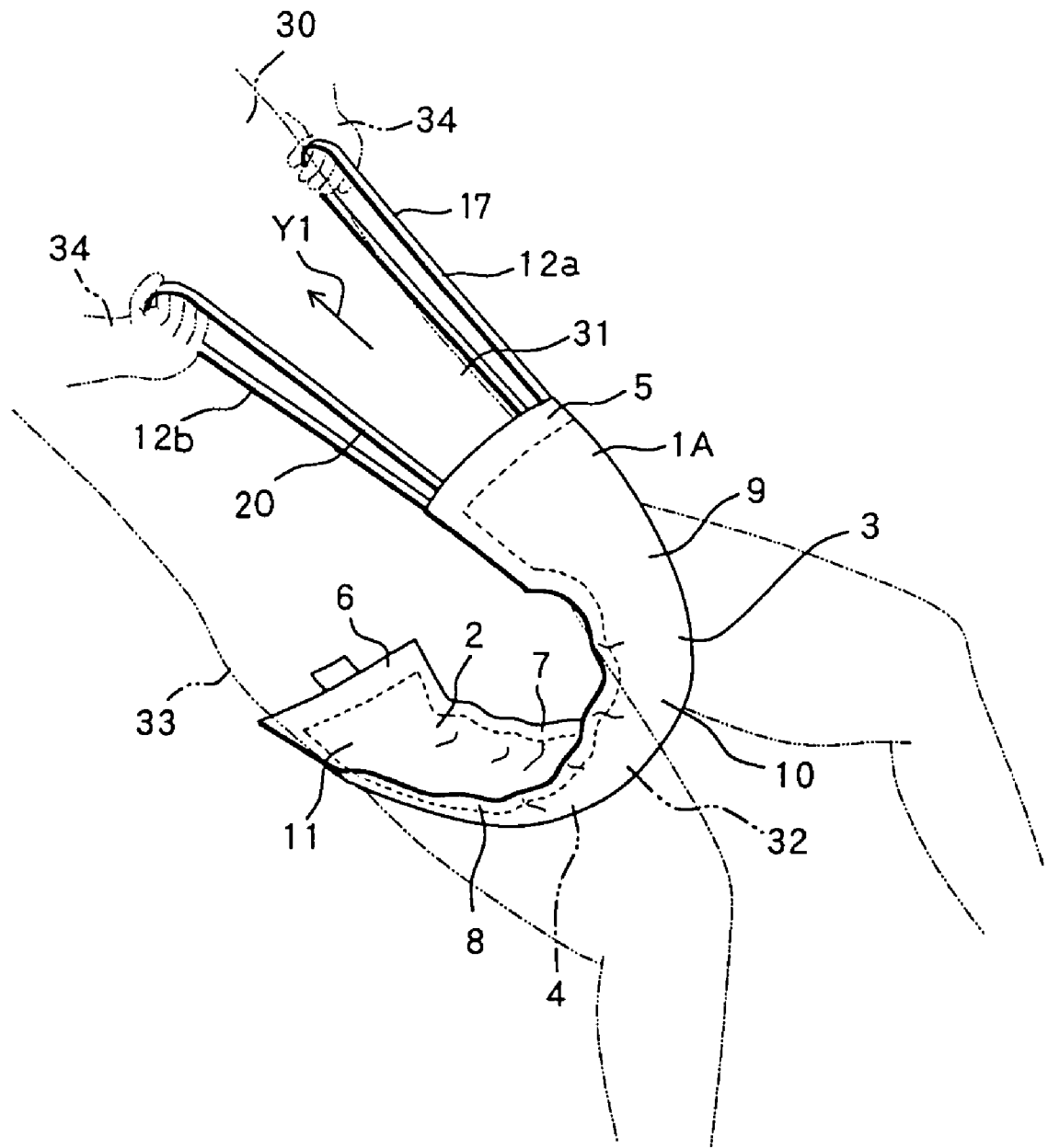
FIG. 5 is a perspective view showing the pad put on a wearer's body.

The pad 1A has a front region 9 destined to cover a belly 31 of a wearer 30, a rear region 11 destined to cover a hip 33 of the wearer 30 and an intermediate region 10 destined to cover a crotch 32 of the wearer 30 when the pad 1A is put on the wearer's body (See FIG. 5). The pad 1A is dimensioned so that a transverse dimension as measured between the side edge margins 7, 8 in the intermediate region 10 is smaller than a transverse dimension as measured between the side edge margins 7, 8 in the front and rear regions 9, 11 and therefore the pad 1A as a whole presents a substantially hourglass-like planar shape. The pad 1A is provided with a pair of straps 12a, 12b by means of which the pad 1A can be pulled in the longitudinal direction and with a tape fastener 13 allowing the pad 1A to be maintained in its folded state (See FIG. 4) until the pad 1A is actually used.

The intermediate region 10 is provided along the side edge margins 7, 8 with a plurality of elastic members 14 attached in a stretched state so as to extend in the longitudinal direction and to be contractible in the longitudinal direction. Specifically, these elastic members 14 are interposed between the top- and backsheets 2, 3 and secured to respective inner surfaces of these sheets 2, 3. Referring to FIG. 1, these elastic members 14 have contracted and thereby caused the pad 1A to curve in the longitudinal direction with the topsheet 2 inside.

The straps 12 comprise a first strap 12a attached to one 7 of the side edge margins 7, 8 so as to extend outward from the end margin 5 of the front region 9 in the longitudinal direction and the second strap 12b is attached to the other side edge margin 8 so as to extend outward from the end margin 5 of the front region 9 in the longitudinal direction. These straps 12a, 12b are made of non-stretchable fibrous nonwoven fabric. These straps 12a, 12b are substantially ring-shaped, respectively.

The first strap 12a has a first inner fixed portion 15 lying on the side edge 7 and secured to the outer surface (facing the wearer's body) of the topsheet 2, a first outer fixed portion 16 lying on the side edge 7 and secured to the outer surface (facing away from the wearer's body) of the backsheet 3, and a first hand-grip 17 extending between the first inner fixed portion 15 and the first outer fixed portion 16. The second strap 12b has a second inner fixed portion 18 lying on the side edge 8 and secured to the outer surface (facing the wearer's body) of the topsheet 2, a second outer fixed portion 19 lying on the side edge 8 and secured to the outer surface (facing away from the wearer's body) of the backsheet 3, and a second hand-grip 20 extending between the second inner fixed portion 18 and the second outer fixed portion 19.

The first and second inner fixed portions 15, 18 extend from the front region 9 toward the intermediate region 10 along the side edge margins 7, 8 of the pad 1A. These inner fixed portions 15, 18 are secured to the topsheet 2 with the elastic members 14 being stretched in the longitudinal direction. In the intermediate region 10, the respective inner fixed portions 15, 18 of these straps 12a, 12b are shrunk in the longitudinal direction as the elastic members 14 contract. The first and second outer fixed portions 16, 19 lie in the front region 9. These inner fixed portions 15, 16 and these outer fixed portions 16, 19 are secured to the top- and backsheets 2, 3 by means of a hot melt adhesive (not shown). Securing of these fixed portions 15, 16, 18, 19 to the top- and backsheets 2, 3 may be achieved by use of not only adhesive but also heat-sealing techniques.

The core 4 extends between the front and rear regions 9, 11 of the pad 1A and secured to the inner surfaces of the top- and backsheets 2, 3. Regarding the thickness, the core 4 is dimensioned so that a thickness dimension L1 as measured between the top- and backsheets 2, 3 in the intermediate region 10 is smaller than thickness dimensions L2, L3 as measured between the top- and backsheets 2, 3 in the front and rear regions 9, 11, respectively. Consequently, a difference in level 21 (see FIG. 2) appears between the front region 9 and the intermediate region 10 as well as between the intermediate region 10 and the rear region 11. Regarding the width, the core 4 is dimensioned so that a transverse dimension L4 as measured between the side edges 4b in the intermediate region 10 of the pad 1A is smaller than a transverse dimension L5 as measured between the side edges 4b in the front and rear regions 9, 11 (See FIG. 3) and therefore the pad 1A as a whole presents a substantially hourglass-like planar shape.

The top- and backsheets 2, 3 are overlaid and joined together along the longitudinally opposite end margins 5, 6 extending outward beyond the longitudinally opposite ends 4a of the core 4 and the transversely opposite side edge margins 7, 8 extending outward beyond the transversely opposite side edges 4b of the core 4.

The tape fastener 13 is provided in the rear region 11 of the pad 1A and extends in the longitudinal direction. The tape fastener 13 has a proximal end 13a fixed to the outer surface (facing away from the wearer's body) of the backsheet 3 and a distal end 13b extending outward from the end margin 6 of the rear region 11 in the longitudinal direction. The distal end 13b is coated with a self-adhesive (not shown). The tape fastener 13 is formed by flexible plastic film.

Joining of the top- and backsheets 2, 3 securing of the elastic members 14 to the top- and backsheets 2, 3 and securing of the core 4 to the top- and backsheets 2, 3 are achieved using a hot melt adhesive (not shown) intermittently applied on the inner surfaces of these sheets 2, 3. Adhesives may be applied on the inner surfaces of these sheets 2, 3 selectively in any one of spiral, zigzag, dotted and striped patterns. It is optionally possible to coat any one of the top- and backsheets 2, 3 with adhesive.

Figure 6:
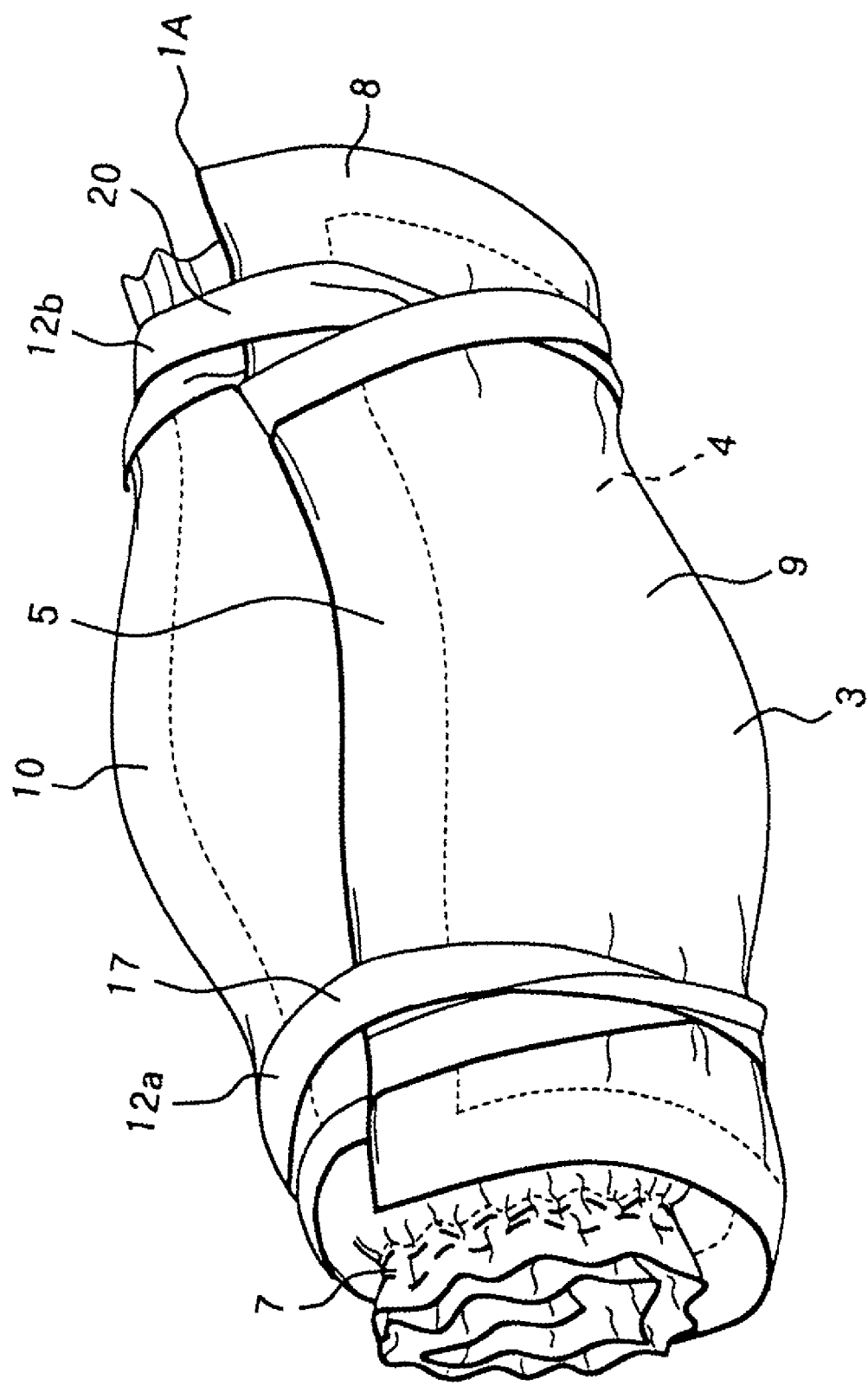
FIG. 6 is a perspective view showing the used pad rolled-up for disposal thereof.

FIG. 4 is a perspective view showing the pad 1A still in a folded state before actual use thereof, FIG. 5 is a perspective view showing the pad 1A put on the wearer's body and FIG. 6 is a perspective view showing the used pad 1A rolled-up for disposal thereof. In FIG. 5, the wearer 30 lying face up is indicated by chain double-dashed lines.

Before actual use of the pad 1A, the intermediate region 10 is folded in two in the longitudinal direction with the topsheet 2 inside so that the front region 9 and the rear region 11 may be placed upon each other as shown in FIG. 4. The distal end 13b of the tape fastener 13 is releasably attached to the outer surface (facing away from the wearer's body) of the backsheet 3 in the front region 9 by means of a self-adhesive. The pad 1A is maintained by this tape fastener 13 in its folded state.

To use the pad 1A, the distal end 13b of the tape fastener 13 is peeled off from the outer surface of the backsheet 3 and the front and rear regions 9, 11 are developed in the longitudinal direction so that these front and rear regions 9, 11 may be separated from each other. An example of the manner in which the care personnel puts the pad 1A on the wearer's body comprises steps of lifting the hip 33 of the wearer 30 lying face upon, placing the rear region 11 of the pad 1A below the hip 33, putting the hip 33 of the wearer 30 down on the rear region 11 and then folding the front region 9 of the pad 1A onto the belly 31 of the wearer 30. In this way, the pad 1A is put on the wearer's body as shown in FIG. 5 in which the pad 1A is curved along the intermediate region 10 so that the front region 9 is placed against the belly 31 of the wearer 30, the rear region 11 is placed against the hip 33 of the wearer 30 and the intermediate region 10 is placed against the crotch region 32 of the wearer 30.

The wearer 30 putting the pad 1A on his or her body may hold the hand-grips 17, 20 of the first and second straps 12a, 12b, respectively, with both hands 34 and may pull these straps 12a, 12b in the longitudinal direction as indicated by an arrow Y1 to place the front and rear regions 9, 11 as well as the intermediate region 10 more closely against the wearer's body and thereby to ensure body fluids to be reliably absorbed by the pad 1A.

In the pad 1A, the elastic members 14 stretch in the longitudinal direction and the side edge margins 7, 8 of the pad 1A in the intermediate region 10 are brought in close contact with the wearer's body as the straps 12a, 12b are pulled outward in the longitudinal direction. Thus it can be avoided that body fluids might leak sideways beyond these side edge margins 7, 8. The strap 12a or 12b may be adjustably pulled to adjust a fitness degree of the side edge margins 7, 8 of the pad 1A to the wearer's body.

Unlike the conventional pad, it is unnecessary for the pad 1A to utilize the shorts by means of which the pad 1A is held in close contact with the body. Specifically, it is unnecessary to place the pad 1A on the shorts but the rear region 11 of the pad 1A may be merely laid under the hip 33 of the wearer 30. Thus the pad 1A can be easily put on the wearer's body and this pad 1A is suitable for the bedridden wearer 30.

In the pad 1A, the level difference 21 appears between the front region 9 and the intermediate region 10 as well as between intermediate region 10 and the rear region 11, so it is ensured that the core 4 is well retained in the crotch 32 of the wearer 30 without any anxiety that the pad 1A might be separated therefrom even if the straps 12a, 12b are powerfully pulled in the longitudinal direction. The pad 1A is dimensioned so that the transverse dimension L4 of the core in the intermediate region 10 of the pad 1A is smaller than those in the front and rear regions 9, 11. Such dimensioning also ensures that the core 4 is well retained in the crotch 32 of the wearer 30 without any anxiety that the pad 1A might be separated therefrom even if the straps 12a, 12b are powerfully pulled in the longitudinal direction.

For disposal of the pad 1A contaminated with body fluids, the pad 1A may be taken off from the wearer's body, the pad 1A may be folded from the rear region 11 onto the front region 9 with the topsheet 2 inside and then the hand-grips 17, 20 of the straps 12a, 12b may be whipped around the outer peripheral surface of the folded pad 1A. The pad 1A is retained by the hand-grips 17, 20 of the straps 12a, 12b in the folded state for disposal.

Figure 7:
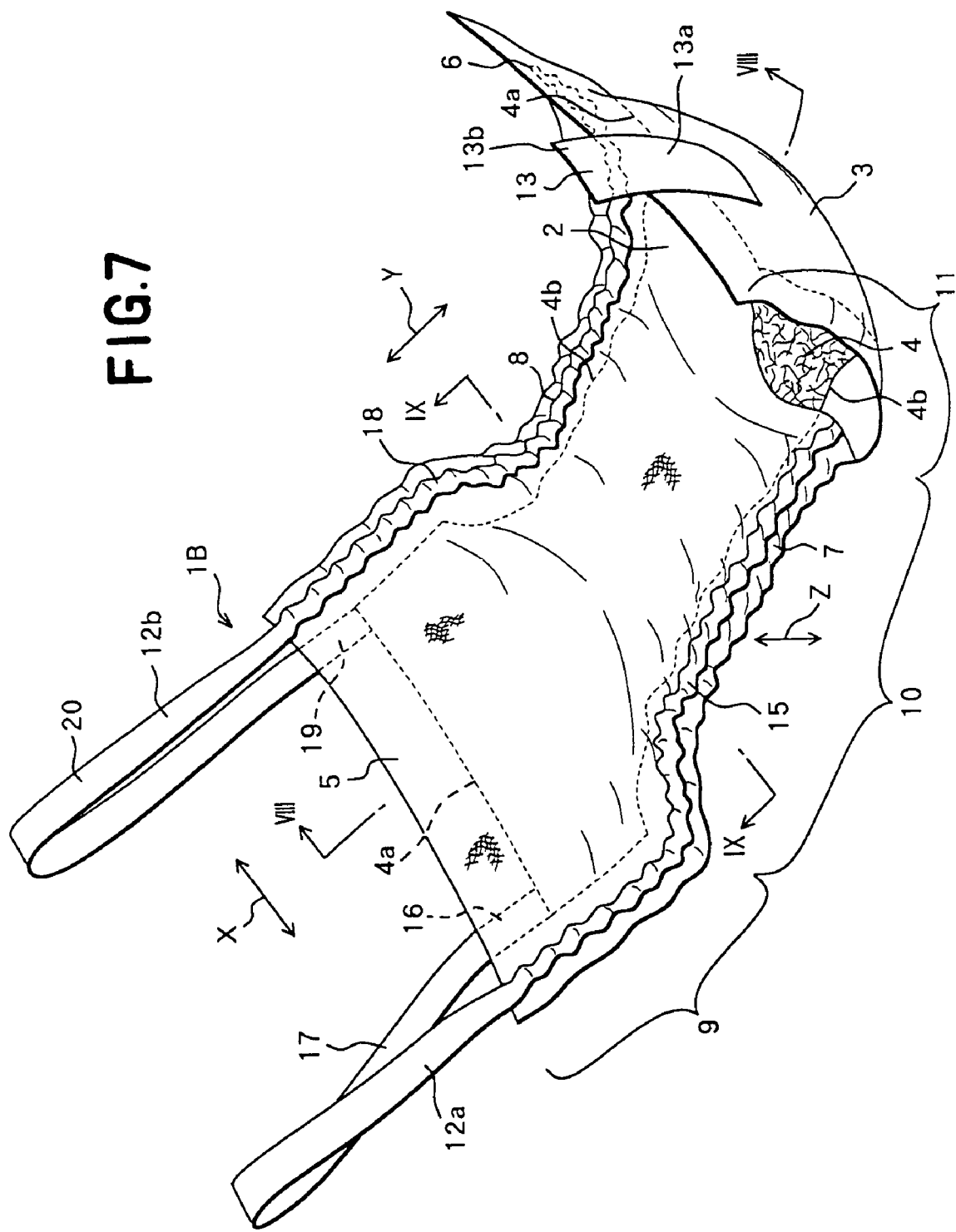
FIG. 7 is a partially cutaway perspective view showing another embodiment of the pad according to the invention.
Figure 8:
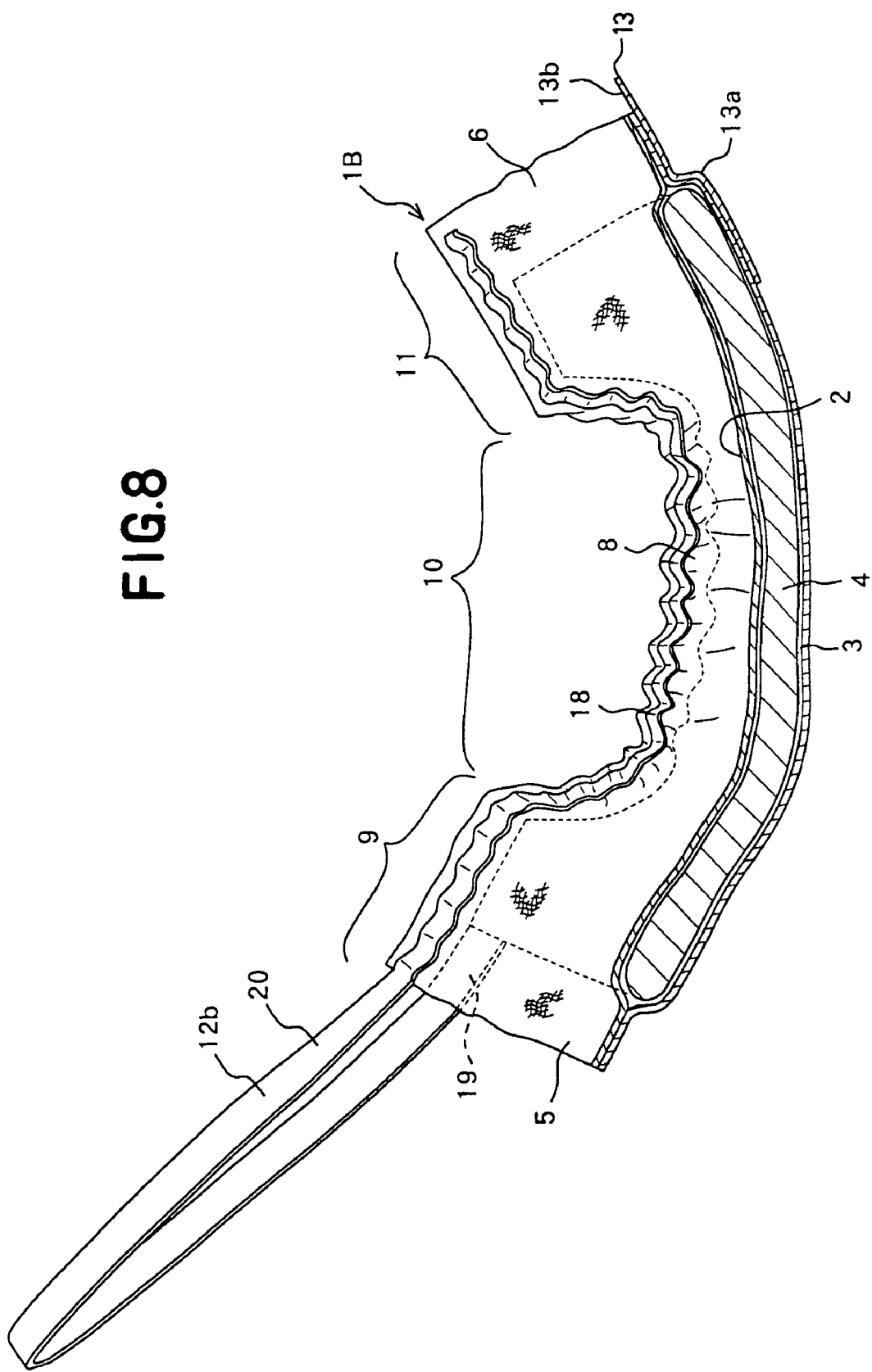
FIG. 8 is a sectional view taken along a line VIII—VIII in FIG. 7.
Figure 9:
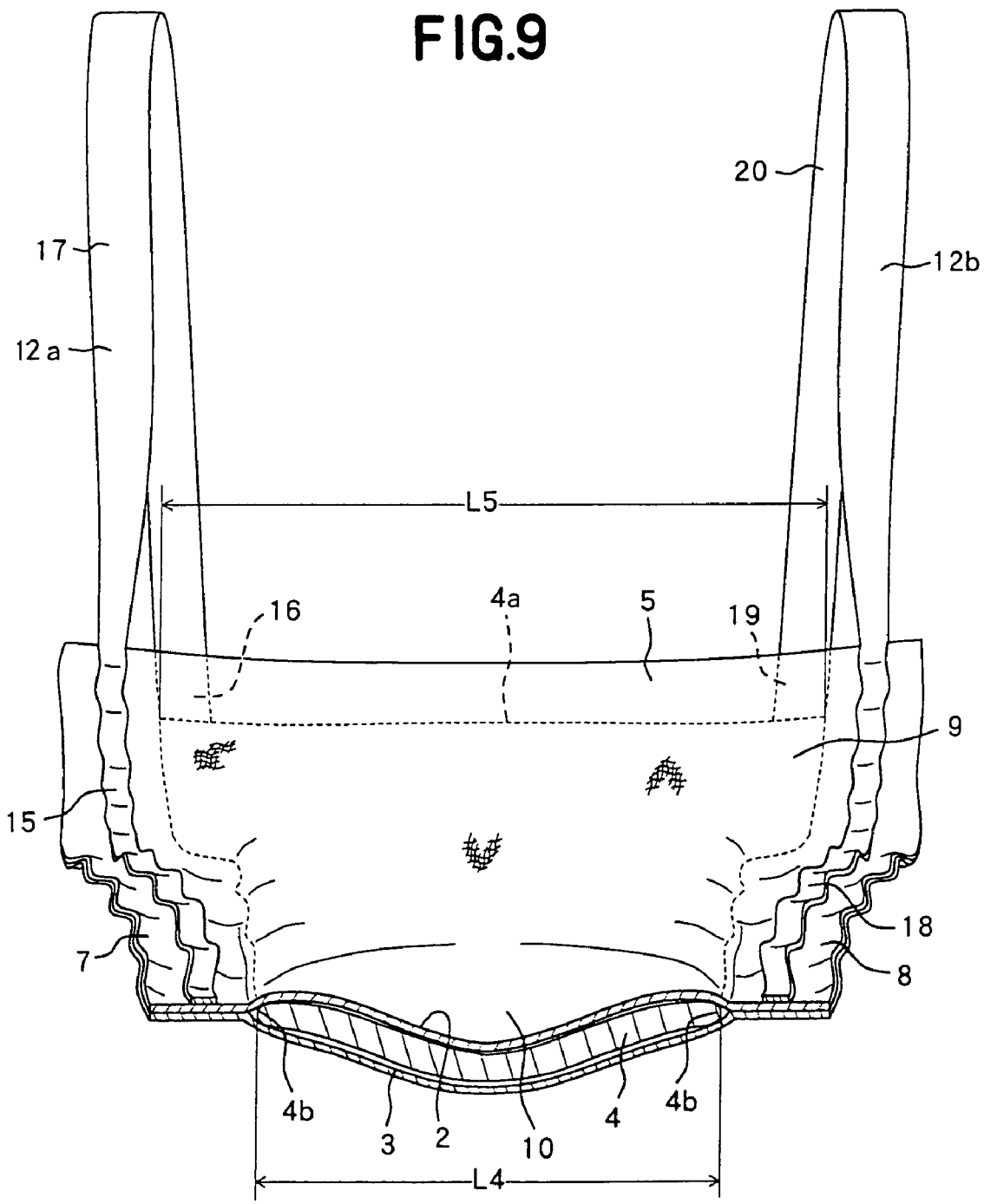
FIG. 9 is a sectional view taken along a line IX—IX in FIG. 7.

FIG. 7 is a partially cutaway perspective view showing a pad 1B according to another embodiment of the invention, FIG. 8 is a sectional view taken along a line VIII—VIII in FIG. 7 and FIG. 9 is a sectional view taken along a line IX—IX in FIG. 7. In FIG. 7, a transverse direction is indicated by an arrow X, a longitudinal direction is indicated by an arrow Y and a thickness direction is indicated by an arrow Z.

The pad 1B comprises the liquid-pervious topsheet 2, the liquid-impervious backsheet 3 and the liquid-absorbent core 4 interposed between the top- and backsheets 2, 3. The pad 1B includes the longitudinally opposite end margins 5, 6, the transversely opposite side edge margins 7, 8, the front region 9 destined to cover the belly 31 of the wearer 30, the rear region 11 destined to cover the hip 33 of the wearer 30 and the intermediate region 10 destined to cover the crotch 32 of the wearer 30. The pad 1B is dimensioned so that the transverse dimension as measured between the side edge margins 7, 8 in the intermediate region 10 is smaller than the transverse dimension as measured between the side edge margins 7, 8 in the front and rear regions 9, 11. The pad 1B is provided with the first and strap straps 12a, 12b adapted to pull the pad 1B in the longitudinal direction and to maintain the pad 1B in its folded state until the pad 1B is actually used.

The first and second straps 12a, 12b are attached to the side edge margins 7, 8, respectively, so as to extend outward from the end margin 5 of the front region 9 in the longitudinal direction. The first strap 12a has the first inner fixed portion 15 lying on the side edge 7 and secured to the outer surface of the topsheet 2, the first outer fixed portion 16 lying on the side edge 7 and secured to the outer surface of the backsheet 3, and the first hand-grip 17 extending between these fixed portions 15, 16. The second strap 12b has the second inner fixed portion 18 lying on the side edge 8 and secured to the outer surface of the topsheet 2, the second outer fixed portion 19 lying on the side edge 8 and secured to the outer surface of the backsheet 3, and the second hand-grip 20 extending between these fixed portions 18, 19. These straps 12a, 12b are formed by elastically stretchable fibrous nonwoven fabric and substantially ring-shaped, respectively.

The first and second inner fixed portions 15, 18 extend from the end margin 5 of front region 9 toward the end margin 6 of the rear region 11 along the side edge margins 7, 8 of the pad 1B. These inner fixed portions 15, 18 are secured in a stretched state to the outer surface of the topsheet 2 and contractible in the longitudinal direction. These outer fixed portions 16, 19 are secured in a non-stretched state to the outer surface of the backsheet 3. In the state shown in FIG. 7, the respective inner fixed portions 15, 18 of the straps 12a, 12b contract in the longitudinal direction and, in consequence, the pad 1B longitudinally curves with the topsheet 2 inside.

The core 4 extends between the front and rear regions 9, 11 of the pad 1B and secured to the inner surfaces of the top- and backsheets 2, 3. Regarding the thickness, the core 4 is dimensioned so that the thickness dimension L1 as measured between the top- and backsheets 2, 3 is substantially uniform in the front and rear regions 9, 11 and the intermediate region 10. Regarding the width, on the other hand, the core 4 is dimensioned so that the transverse dimension L4 as measured between the side edges 4b in the intermediate region 10 of the pad 1B is smaller than the transverse dimension L5 as measured between the side edges 4b in the front and rear regions 9, 11. The top- and backsheets 2, 3 are overlaid and joined together at the longitudinally opposite end margins 5, 6 and the transversely opposite side edges 7, 8. The tape fastener 13 is attached to the outer surface of the backsheet 3 in the rear region 11 of the pad 1B Both the folded posture of the pad 1B before actual use and the steps followed to put the pad 1B on the wearer's body are similar to those as illustrated in FIGS. 4 and 5, respectively, and the folded and whipped posture of the used pad 1B for disposal is similar to that as illustrated in FIG. 6. Therefore, detailed description of these postures and steps will be not repeated.

The wearer 30 putting the pad 1B on his or her body may hold the hand-grips 17, 20 of the first and second straps 12a, 12b, respectively, with both hands 34 and may pull these straps 12a, 12b in the longitudinal direction to place the front and rear regions 9, 11 as well as the intermediate region 10 more closely against the wearer's body and thereby to ensure body fluids to be reliably absorbed by the pad 1B. In the pad 1B, the inner fixed portions 15, 18 of the straps 12a, 12b, respectively, stretch in the longitudinal direction and these inner fixed portions 15, 18 are brought in close contact with the wearer's body as the straps 12a, 12b are pulled in the longitudinal direction. Thus it can be avoided that body fluids might leak sideways beyond these side edge margins 7, 8.

In the pad 1B, the inner fixed portions 15, 18 of the respective straps 12a, 12b extend between the front and rear regions 9, 11, so not only the front region 9 but also the intermediate region 10 and the rear region 11 are pulled in the longitudinal direction as the straps 12a, 12b are pulled. Thereby the front and rear regions 9, 11 as well as the intermediate region 10 can be reliably brought in close contact with the wearer's body. In addition, the strap 12a or 12b may be adjustably pulled to adjust a fitness degree of the inner fixed portions 15, 18 of these straps 12a, 12b as well as the side edge margins 7, 8 of the pad 1B to the wearer's body.

It is unnecessary for the pad 1B to utilize the shorts by means of which the pad 1B is held in close contact with the body. Specifically, it is unnecessary to place the pad 1B on the shorts but the rear region 11 of the pad 1B may be merely laid under the hip 33 of the wearer 30. Thus the pad 1B can be easily put on the wearer's body.

Figure 10:
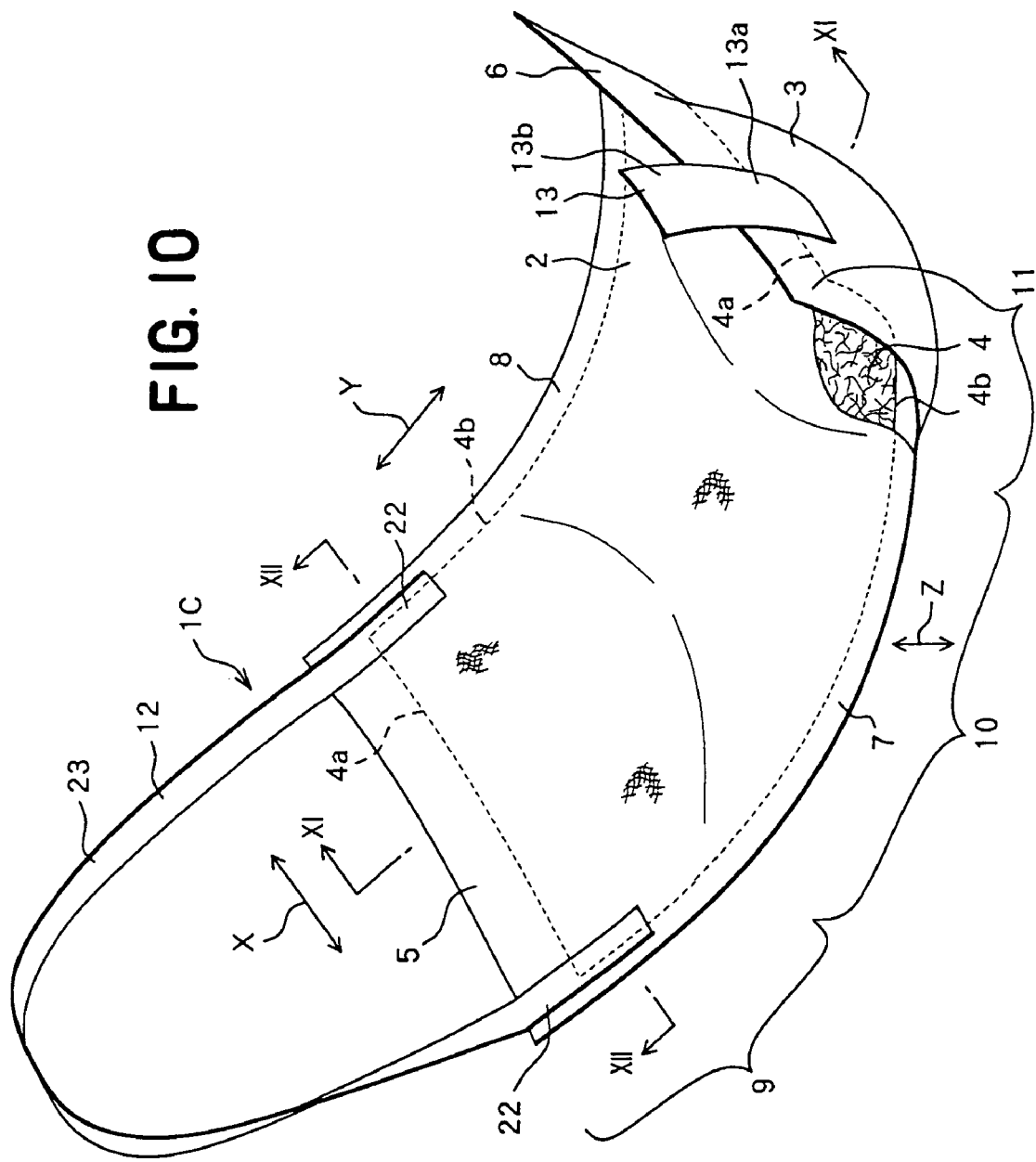
FIG. 10 is a partially cutaway perspective view showing still another embodiment of the pad according to the invention.
Figure 11:
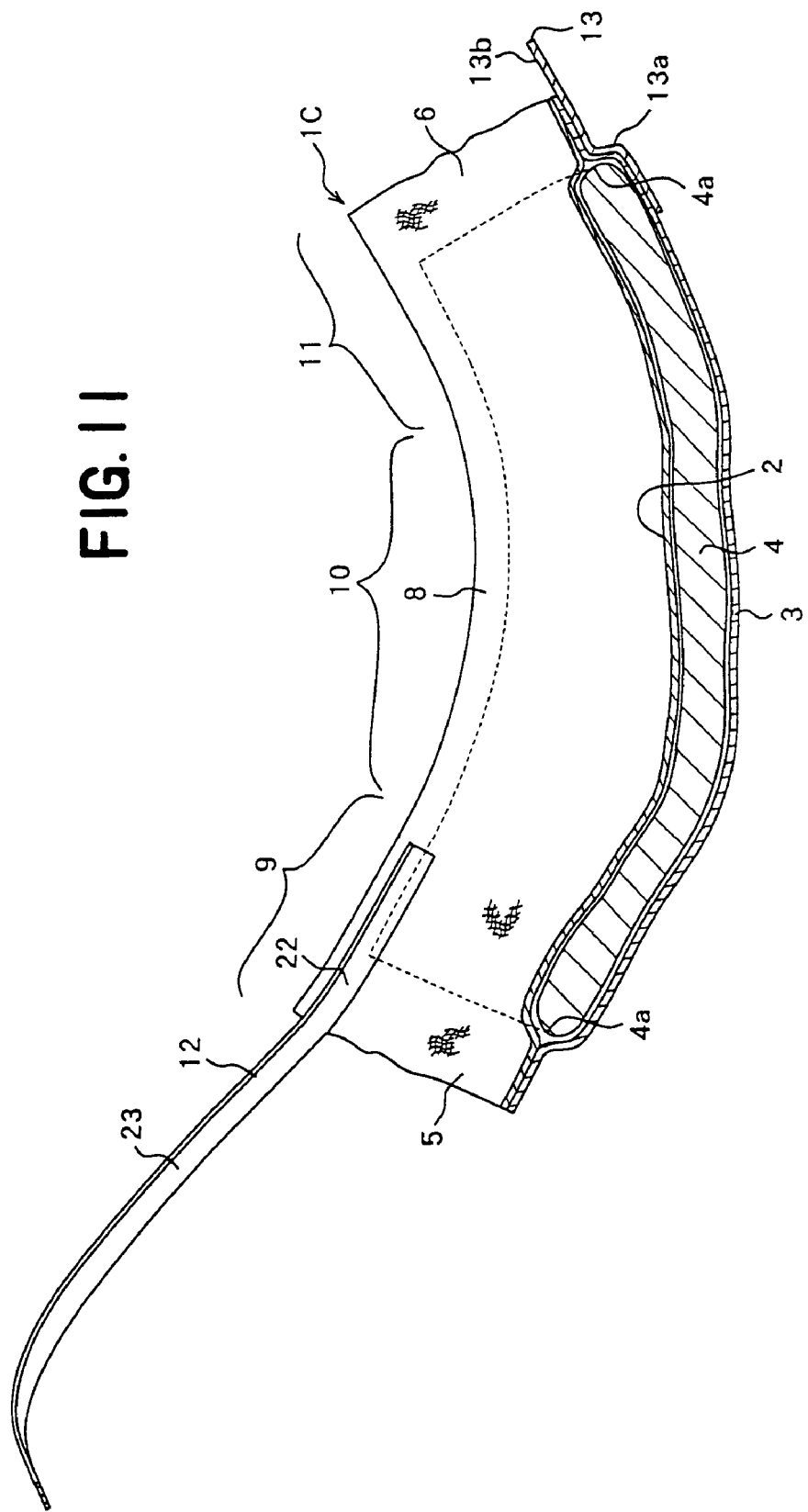
FIG. 11 is a sectional view taken along a line XI—XI in FIG. 10.
Figure 12:
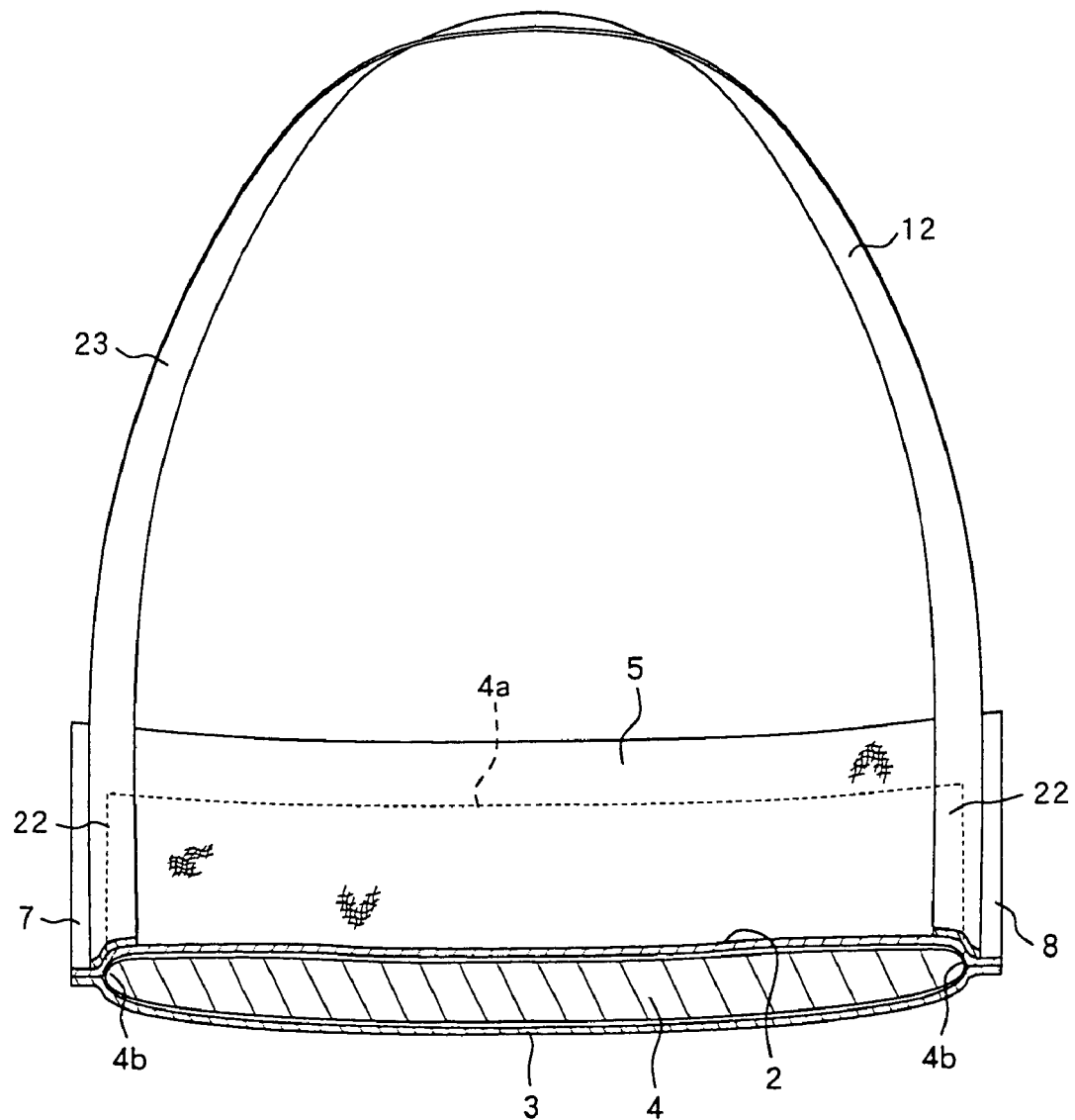
FIG. 12 is a sectional view taken along a line XII—XII in FIG. 10.

FIG. 10 is a partially cutaway perspective view showing a diaper 1C according to still another embodiment of the invention, FIG. 11 is a sectional view taken along a line XI—XI in FIG. 10 and FIG. 12 is a sectional view taken along a line XII—XII in FIG. 10. In FIG. 10, a transverse direction is indicated by an arrow X, a longitudinal direction is indicated by an arrow Y and a thickness direction is indicated by an arrow Z.

The pad 1C comprises the liquid-pervious topsheet 2, the liquid-impervious backsheet 3 and the liquid-absorbent core 4 interposed between the top- and backsheets 2, 3. The pad 1C includes the longitudinally opposite end margins 5, 6, the transversely opposite side edge margins 7, 8, the front region 9 destined to cover belly 31 of the wearer 30, the rear region 11 destined to cover hip 33 of the wearer 30 and the intermediate region 10 destined to cover crotch 32 of the wearer 30 when the pad 1C is put on the wearer's body. The pad 1C is dimensioned so that the transverse dimension as measured between the side edge margins 7, 8 in the intermediate region 10 is substantially same as the transverse dimension as measured between the side edge margins 7, 8 in the front and rear regions 9, 11 and therefore the pad 1C as a whole presents a rectangular planar shape which is relatively large in the longitudinal direction. The pad 1C is provided with a single strap 12 by means of which the pad 1C can be pulled in the longitudinal direction and with a tape fastener 13 allowing the pad 1C to be maintained in its folded state until the pad 1C is actually used.

The single strap 12 has a pair of inner fixed portions 22 lying on the both side edge margins 7, 8 in the front region 9 and secured to the outer surface of the topsheet 2 and a hand-grip 23 extending between these inner fixed portions 22. The inner fixed portions 22 respectively overlap the side edges 4b of the core 4. The strap 12 is made of non-stretchable fibrous nonwoven fabric. This strap 12 also is substantially ring-shaped.

The core 4 extends between the front and rear regions 9, 11 of the pad 1C and secured to the inner surfaces of the top- and backsheets 2, 3. Regarding the thickness, the core 4 is dimensioned so that a thickness dimension as measured between the top- and backsheets 2, 3 in the intermediate region 10 and the thickness dimensions as measured between the top- and backsheets 2, 3 in the front and rear regions 9, 11, respectively are substantially uniform. Regarding the width, the core 4 is dimensioned so that a transverse dimension as measured between the side edges 4b in the intermediate region 10 of the pad 1C is substantially equal to a transverse dimension as measured between the side edges 4b in the front and rear regions 9, 11. The top- and backsheets 2, 3 are overlaid and joined together along the longitudinally opposite end margins 5, 6 extending outward beyond the transversely opposite ends 4a of the core 4 and the transversely opposite side edge margins 7, 8 extending outward beyond the transversely opposite side edges 4b of the core 4. The tape fastener 13 is attached to the outer surface of the backsheet 3 in the rear region 11 of the pad 1C.

Figure 13:
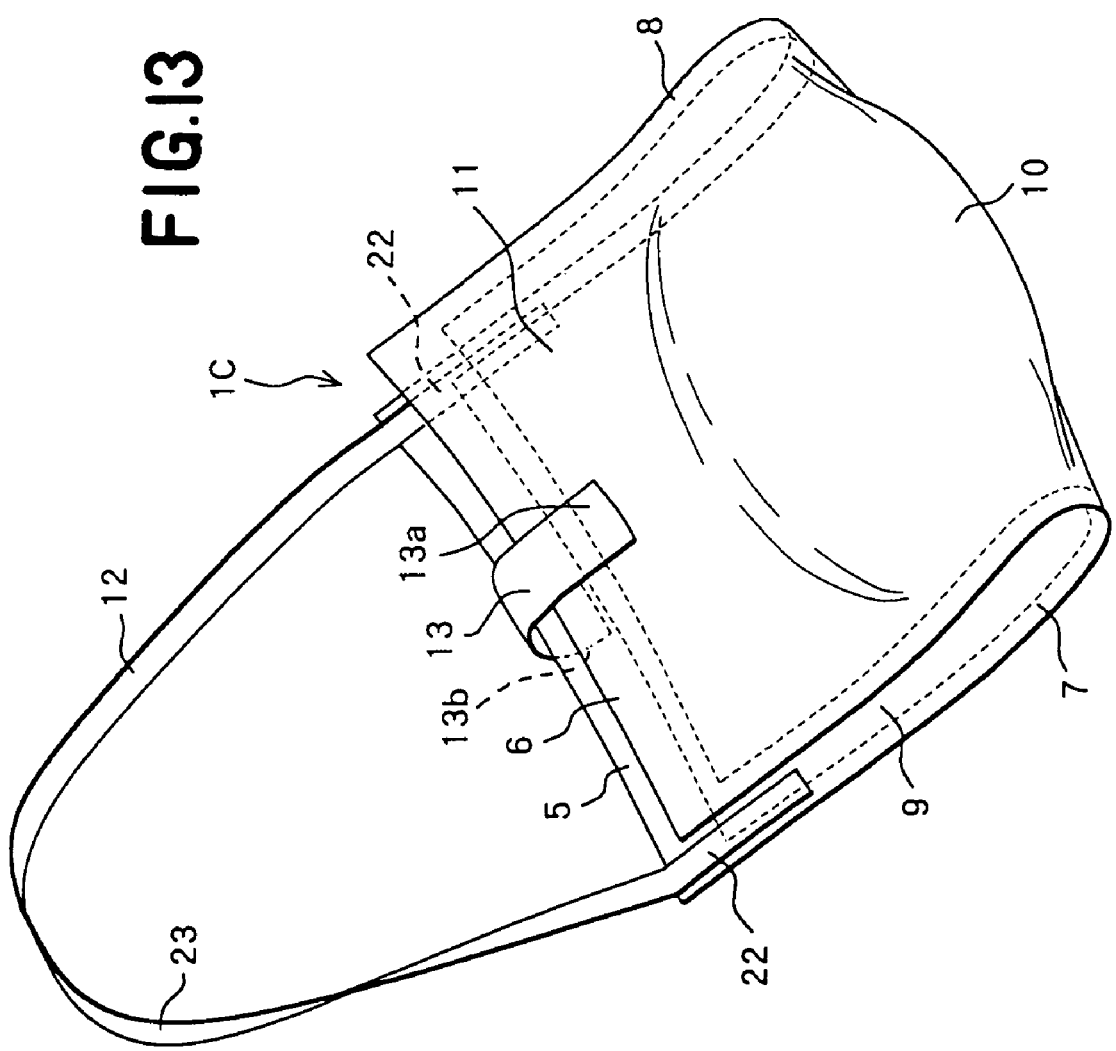
FIG. 13 is a perspective view showing the pad still in a folded state before actual use thereof.
Figure 14:
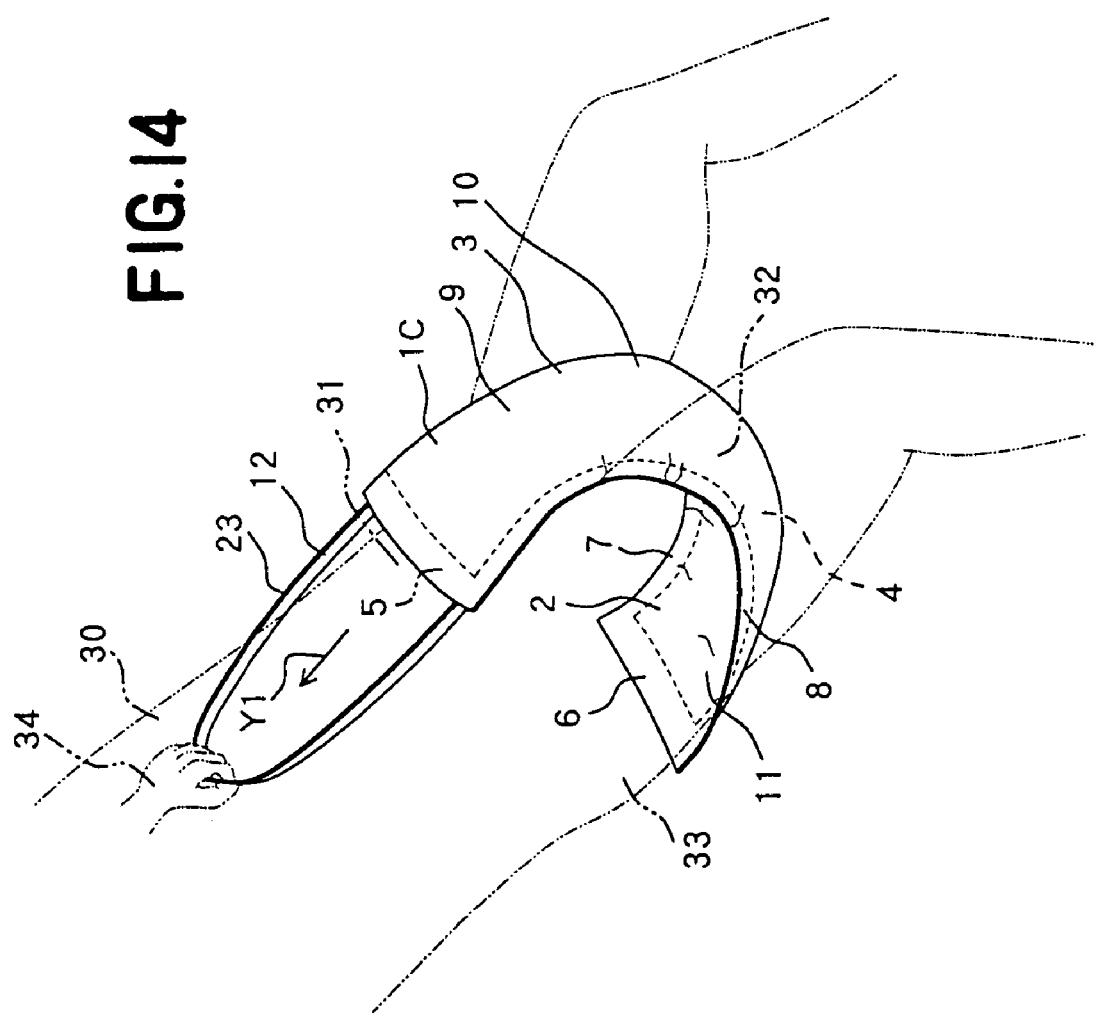
FIG. 14 is a perspective view showing the pad put on the wearer's body.
Figure 15:
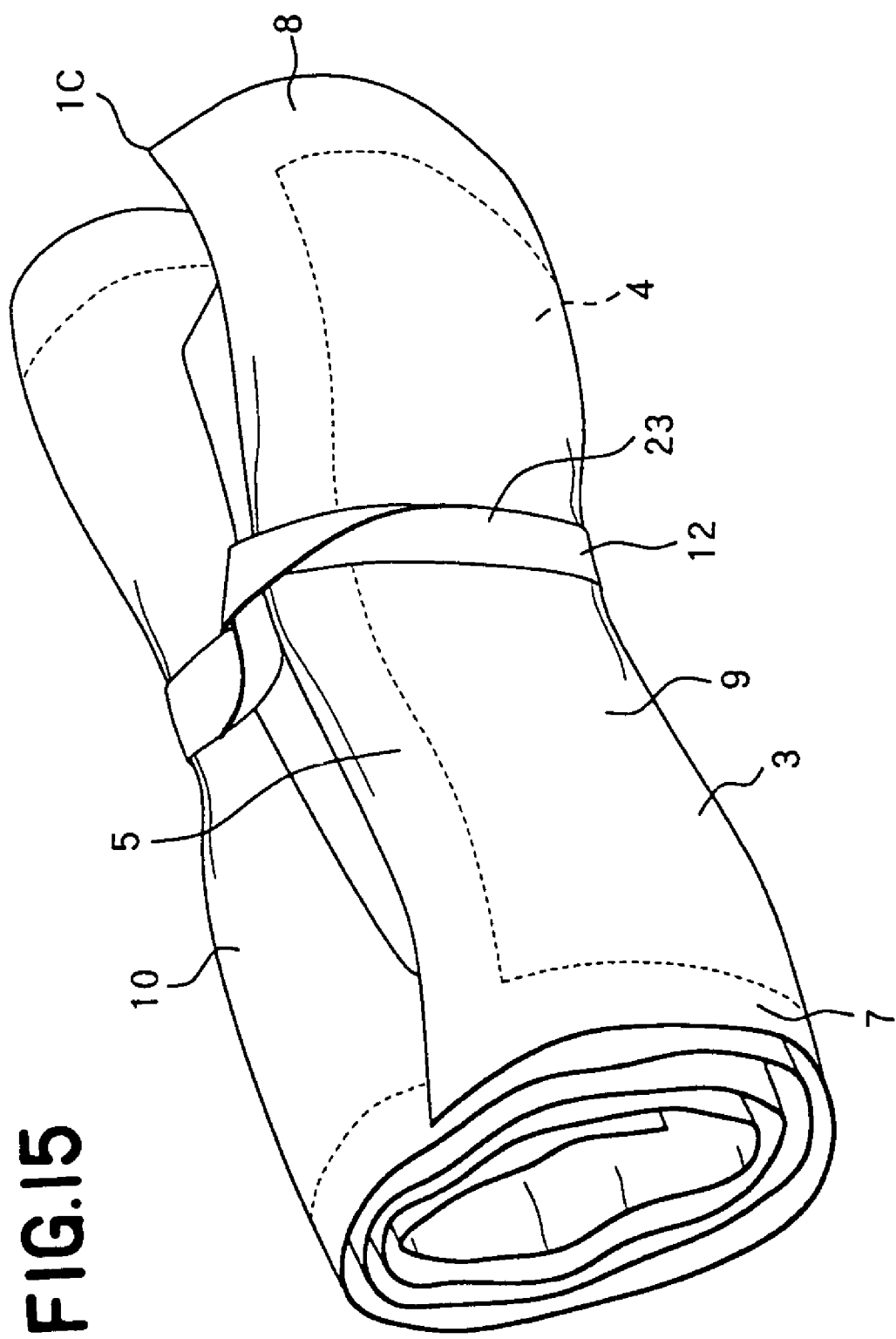
FIG. 15 is a perspective view showing the used pad rolled-up for disposal thereof.

FIG. 13 is a perspective view showing the pad 1C still in folded state before actual use thereof, FIG. 14 is a perspective view showing the pad 1C put on the wearer's body and FIG. 15 is a perspective view showing the used pad 1C rolled-up for disposal thereof. In FIG. 14, the bedridden wearer 30 is indicated by chain double-dashed lines.

Before actual use of the pad 1C, the intermediate region 10 is folded in two in the longitudinal direction with the topsheet 2 inside so that the front region 9 and the rear region 11 may be placed upon each other as shown in FIG. 13. The distal end 13b of the tape fastener 13 is releasably attached to the outer surface of the backsheet 3 in the front region 9 by means of a-self-adhesive (not shown).

The pad 1C may be put on the wearer's body in the same manner as the case of the embodiment shown in FIG. 5. The pad 1C is put on the wearer's body as shown in FIG. 14 in which the pad 1C is curved along the intermediate region 10 so that the front region 9 is placed against the belly 31 of the wearer 30, the rear region 11 is placed against the hip 33 of the wearer 30 and the intermediate region 10 is placed against the crotch region 32 of the wearer 30.

The wearer 30 putting the pad 1C on his or her body may hold the hand-grip 23 of the strap 12 with one hand 34 and may pull the strap 12 in the longitudinal direction as indicated by an arrow Y1 to place the front and rear regions 9, 11 as well as the intermediate region 10 more closely against the wearer's body and thereby to ensure body fluids to be reliably absorbed by the pad 1C. It is unnecessary to place the pad 1A on the shorts but the rear region 11 of the pad 1C may be merely laid under the hip 33 of the wearer 30. Thus the pad 1C can be easily put on the wearer's body.

For disposal of the pad 1C contaminated with body fluids, the pad 1C may be folded from the rear region 11 onto the front region 9 with the topsheet 2 inside and then the hand-grip 23 of the strap 12 may be whipped around the outer peripheral surface of the folded pad 1C. The pad 1C is retained by the strap 12 in the folded state for disposal.

A stock material for the topsheet 2 may be selected from the group of a hydrophilic fibrous nonwoven fabric, a hydrophobic fibrous nonwoven fabric having a plurality of apertures and a finely perforated plastic film. A stock material for the backsheet 3 may be selected from the group consisting of a hydrophobic fibrous nonwoven fabric, a breathable but liquid-impervious plastic film, a composite nonwoven fabric comprising two or more layers of hydrophobic fibrous nonwoven fabric and a composite sheet comprising a hydrophobic fibrous nonwoven fabric laminated with a breathable but liquid-impervious plastic film. The straps 12, 12a, 12b may be formed also by an inelastic plastic sheet or a stretchable plastic sheet.

The fibrous nonwoven fabric may be selected from the group consisting of a spun lace nonwoven fabric, a needle punch nonwoven fabric, a melt blown nonwoven fabric, a thermal bond nonwoven fabric, a spun bond nonwoven fabric and a chemical bond nonwoven fabric and an air-through nonwoven fabric. Component fibers of the nonwoven fabric may be selected from the group consisting of polyolefine-, polyester- and polyamide-based fibers and sheath-core-type conjugated fibers or side-by-side-type conjugated fibers of polyethylene/polypropylene or polyethylene/polyester.

A stock material for an elastically stretchable fibrous nonwoven fabric may be selected from the group consisting of a melt blown nonwoven fabric and a spun bond nonwoven fabric. As component fibers of such elastically stretchable nonwoven fabrics, it is possible to use the elastically stretchable fibers obtained by melt spinning thermoplastic elastomer resin. It is also possible to use, as the elastically stretchable fibrous nonwoven fabric, a composite nonwoven fabric comprising a stretchable and hydrophobic fibrous nonwoven fabric of thermoplastic elastomer resin fiber and a hydrophobic fibrous nonwoven fabric of crimped fibers obtained by melt spinning thermoplastic synthetic resin selected from the group consisting polypropylene, polyethylene and polyester laid on single side or both sides of the stretchable and hydrophobic fibrous nonwoven fabric.

The core 4 is a mixture of fluff pulp and super-absorbent polymer particles or a mixture of fluff pulp, super-absorbent polymer particles and thermoplastic synthetic resin fibers, in both cases, compressed to a predetermined thickness. Preferably, the core 4 is entirely covered with a liquid-pervious sheet such as a tissue paper or a hydrophilic fibrous nonwoven fabric in order to prevent the core 4 from getting out of shape and at the same time in order to prevent the polymer particles from falling off. The polymer particles may be selected from the group consisting of starch-based polymer particles, cellulose-based polymer particles or synthetic polymer particles.

For disposal of the pad 1A, 1B illustrated as the specific embodiments, contaminated with body fluids, it is also possible to fold the pad 1A, 1B, from the front region 9 onto the rear region 11 and then to anchor the distal end 13b of the tape fastener 13 on the outer surface of the backsheet 3. The pad 1A, 1B are retained by the tape fastener 13 in the rolled up state for disposal.

With the disposable body fluid absorbent pad according to the invention, the strap may be pulled in the longitudinal direction to place the front and rear regions as well as the intermediate region closely against the wearer's body and thereby to ensure body fluids to be reliably absorbed by the pad. It is unnecessary to place the pad on the shorts but the rear region of the pad may be merely laid under the hip of the wearer. Thus the pad can be easily put on the wearer's body and this pad is suitable for the bedridden wearer.

In the case of the pad in which the strap comprises the first and second straps, these straps may be pulled in the longitudinal direction to place the front and rear regions as well as the intermediate region closely against the wearer's body. In addition, these straps may be adjustably pulled to adjust a degree of fitness of the side edge margins of the pad to the wearer's body.

In the case of the pad in which the inner fixed portions of the straps extending from the end margin of the front region toward the end margin of the rear region along the side edge margins, not only the front region but also the intermediate region and the rear region are pulled in the longitudinal direction and thereby these regions are reliably brought in close contact with the wearer Is body as the straps are pulled.

In the case of the pad in which the elastic members extending in the longitudinal direction are attached to the side edge margins so that these elastic members are contractible in the longitudinal direction, the straps may be pulled outward in the longitudinal direction to stretch the elastic members in the longitudinal direction and thereby to bring the side edge margins of the pad in close contact with the wearer's body. In this way, it is possible to prevent body fluids from leaking sideways beyond the side edge margins of the pad.

In the case of the pad in which the straps are elastically stretchable, the inner fixed portions of the respective straps are stretched in the longitudinal direction and these inner fixed portions tightly fit to the wearer's body as the elastic members are stretched in the longitudinal direction. In this way, it is possible to prevent body fluids from leaking sideways beyond the side edge margins of the pad.

In the case of the pad in which the thickness of the core as measured between the top- and backsheets is smaller in the intermediate region than in the front and rear regions, a level difference appears between the front region and the intermediate region as well as between the intermediate region and the rear region. Such dimensioning ensures that the core is well retained in the crotch of the wearer without any anxiety that the pad might be separated therefrom even if the straps are powerfully pulled in the longitudinal direction.

In the case of the pad in which the transverse dimension of the core is smaller in the intermediate region than in the rear region, the core is well retained in the crotch of the wearer without any anxiety that the pad might be separated therefrom even if the straps are powerfully pulled in the longitudinal direction.

In the case of the pad in which the tape fastener extending in the longitudinal direction is attached to the pad in the rear region, the distal end of this tape fastener may be releasably attached to the outer surface of the backsheet in the front region to maintain the pad in its folded state until the pad is actually used.

What is claimed is:

1. A disposable body fluid absorbent pad comprising:
a top surface facing a wearer's body;
a back surface facing away from said wearer's body;
a liquid-absorbent core interposed between said top and back surfaces and having longitudinally opposite end margin portions extending in a transverse direction and defining peripheral longitudinal edge portions of the liquid-absorbent core and transversely opposite side edge margin portions extending in a longitudinal direction and defining peripheral transverse edge portions of the liquid-absorbent core;
a front region destined to cover a wearer's belly;
a rear region destined to cover a wearer's hip;
an intermediate region destined to cover a wearer's crotch when said pad is put on said wearer's body; and
a strap extending longitudinally outward from the front region for pulling said pad in said longitudinal direction, said strap having inner fixed portions lying on and extending along a length of said side edge margin portions and secured to said pad on a surface facing said wearer's body and a hand-grip extending between said inner fixed portions.

2. The pad according to claim 1, wherein said strap comprises:
a first strap attached to one of said side edge margin portions so as to extend outward from said end margin of said front region in said longitudinal direction; and
a second strap is attached to said other side edge margin portion so as to extend outward from said end margin of said front region in said longitudinal direction,
said first strap having an inner fixed portion lying on one of said side edge margin portions and secured to said pad on said surface facing said wearer's body, an outer fixed portion lying on said other side edge margin portion and secured to said pad on said surface facing away from said wearer's body and a hand-grip extending between said inner fixed portion and said outer fixed portion and,
said second strap having an inner fixed portion lying on said other side edge margin portion and secured to said pad on said surface facing said wearer's body, an outer fixed portion lying on said other side edge margin portion and secured to said pad on said surface facing away from said wearer's body and a hand-grip extending between said inner fixed portion and said outer fixed portion.

3. The pad according to claim 2, wherein said inner fixed portions of said straps extend from said end margin of said front region toward said end margin of said rear region along said side edge margins.

4. The pad according to claim 3, further comprising elastic members extending at least in said intermediate region of said side margin portions of said pad so that said elastic members are contractible in said longitudinal direction and said inner fixed portions of said straps contract in said longitudinal direction as said elastic members contract.

5. The pad according to claim 3, wherein said straps are elastically stretchable and said inner fixed portions of said straps are secured to said pad on said surface facing said wearer's body so that said inner fixed portions are contractible.

6. The pad according to claim 1, wherein said top surface comprises a liquid-pervious topsheet and said back surface comprises a liquid-impervious backsheet.

7. The pad according to claim 1, wherein a thickness dimension of said core between said top and back surfaces as measured in said intermediate region is smaller than a thickness as measured in said front and rear regions.

8. The pad according to claim 1, wherein a transverse dimension of said core between the side edge margins as measured in said intermediate region is smaller than a transverse dimension measured in said front and rear regions.

9. The pad according to claim 1, wherein said pad is provided in said rear region with a tape fastener having a proximal end fixed to said pad on said surface facing away from said wearer's body in said rear region and a distal end extending outward from said end margin of said rear region in said longitudinal direction and configured to be releasably attached to said pad on said surface facing away from said wearer's body.

10. The pad according to claim 9, wherein said intermediate region of said pad is folded in said longitudinal direction with said top surface inside so that said front and rear regions may be placed upon each other and said distal end of said tape fastener is releasably attached to said pad on said surface facing away from said wearer's body in said front region so as to maintain said pad in a folded state.

* * * * *